United States Patent [19]

Posthuma et al.

[11] 4,232,003

[45] Nov. 4, 1980

[54] SYNTHETIC PHYSIOLOGICAL MUCUS

[76] Inventors: Albert E. Posthuma, 3520 Burton Ridge, Apt. D, Grand Rapids, Mich. 49506; Robert C. Woodhouse, 1664 Alexander, S.E., Grand Rapids, Mich. 49506

[21] Appl. No.: 635,436

[22] Filed: Nov. 26, 1975

Related U.S. Application Data

[63] Continuation-in-part of Ser. No. 470,522, May 16, 1974, abandoned, which is a continuation-in-part of Ser. No. 332,933, Feb. 16, 1973, abandoned.

[51] Int. Cl.³ .............................................. A61K 31/78
[52] U.S. Cl. ........................................ 424/81; 424/78; 424/DIG. 14
[58] Field of Search .............. 424/78, 80, 81, DIG. 14

[56] References Cited

U.S. PATENT DOCUMENTS

| | | | |
|---|---|---|---|
| 3,072,536 | 1/1963 | Pye | 424/81 X |
| 3,590,124 | 6/1971 | Hoyt | 424/78 |
| 3,767,789 | 10/1973 | Rankin | 424/78 |

FOREIGN PATENT DOCUMENTS

| | | | |
|---|---|---|---|
| 46-34632 | 11/1971 | Japan | 424/81 |
| 831856 | 4/1960 | United Kingdom | 424/81 |

OTHER PUBLICATIONS

Isacoff, Cos. & Perf., vol. 88, Feb., 1973, pp. 35–37.
Schimmel Briefs, Schimmel & Co, Newburgh, NY No. 339, Jun., 1963, 1 p.
Davidson, Water-Soluble Resins, Reinhold Book Corp. NY, 2nd Ed., 1962 pp. 154–163, 175–189.

*Primary Examiner*—Anna P. Fagelson
*Attorney, Agent, or Firm*—Price, Heneveld, Huizenga & Cooper

[57] ABSTRACT

A synthetic physiological mucus having particular usefulness as a vaginal and surgical lubricant, based upon a pituitous aqueous solution of a high molecular weight polyacrylamide.

7 Claims, No Drawings

SYNTHETIC PHYSIOLOGICAL MUCUS

CROSS REFERENCE TO RELATED APPLICATION

This application is a continuation-in-part of pending application Ser. No. 470,522 filed May 16, 1974 for Synthetic Physiological Mucus, which application was a continuation-in-part of application Ser. No. 332,933 filed Feb. 16, 1973 for Synthetic Physiological Mucus both now abandoned.

BACKGROUND OF THE INVENTION

This invention relates to synthetic physiological mucus especially for use as a vaginal and surgical lubricant, and having characteristics resembling those of natural mucus.

Certain medical and/or physical conditions cause the use of vaginal and surgical lubricants to be advisable or even necessary. Typically, the use of a vaginal lubricant is important under conditions of postmenopausal vaginal atrophy or post hysterectomy, or generally of inadequate ability for normal quantities of mucus production. Medical instrument insertion into bodily orifices also requires use of a proper lubricant, as for proctological examination and/or treatment, tracheoscopic examination, and the like.

Typical lubricants in use today as for vaginal use do not posses special characteristics rendering them particularly suitable for this usage, but rather constitute common lubricants such as petrolatum jelly, propylene glycol, glycerine, and methyl cellulose. These lubricants have characteristics different from those of normal mucus and consequently are less than totally satisfactory for physiological usage.

SUMMARY OF THE INVENTION

The present invention occured as a result of the applicants herein, a gynecologist and a chemist, realizing the shortcomings of present physiological lubricants, and discovering a novel vaginal and surgical lubricant having characteristics remarkably similar to those of natural mucus.

Objects of this invention are to provide a synthetic physiological mucus, and to provide a lubricant particularly suited as a vaginal and surgical lubricant, and having characteristics closely comparable to those of natural mucus. The lubricant constitutes a synthetic physiological mucus for gynecological, surgical, and general medical usage. It is stainless, odorless, tasteless, water soluble, and non-toxic. The composition as prepared is sterile and bacteriostatic, and its pH is readily alterable to be ideally suited for vaginal use.

The invention is based upon an aqueous solution of a high molecular weight polyacrylamide. The mucus-like product possesses the unusual combination of high lubricity, pituitousness, and clinginess characteristics of natural mucus. It is a crystal clear solution, it can be sterilized in an autoclave, and has substantial durability, both in terms of shelf life and use.

DESCRIPTION OF THE PREFERRED EMBODIMENT

The present invention is based upon the finding that common lubricants are not really adequate substitutes, physiologically, for natural mucus. The supply of vaginal mucus in particular can be inadequate, particularly in the years following a hysterectomy or following menopause. Unfortunately, this seemingly minor difficulty can gradually, or in some instances rapidly, result in disastrous consequences in a marriage relationship. The use of common lubricants has been of some assistance, but known common lubricants really lack important characteristics of natural mucus. Specifically, common lubricants such as petrolatum jelly, glycerine, etc., while having some lubricity, do not possess the combination of high lubricity or slipperiness plus the high adherence and lubricious film forming capacity, with clinging quality of mucus. Consequently, the effect is substantially different in a definite but rather inexplicable way.

Artificial lubricants for other bodily orifices seem to have comparable deficiencies, the problem being particularly acute during medical examinations, surgical procedures, and the like. Catheter insertion and the like present particular problems because of pain and discomfort caused by ineffective lubrication using present technology. And, application of the lubricant prior to use is messy at best.

The applicants herein, based upon their determination that this inadequacy constituted a significant barrier to the comfort, well-being and happiness of persons involved, began a search for a synthetic mucus useful as an effective substitute pituitous lubricant. This search resulted in the discovery of a material having qualities rendering it particularly suitable as synthetic mucus and as vaginal, medical and surgical lubricants.

This material has the important combination of characteristics of high lubricity or slipperiness and exceptional adherence tenacity or clinginess, capable of lubricious film forming capacity as well as being stainless, odorless, and water soluble. It has pituitousness, tending to form long filaments as an object is withdrawn from the material. Further, the lubricant is capable of pH adjustment to the desirable range of about 5–8 without loss of these characteristics, is basically tasteless and is non-toxic. It can be rendered initially sterile and bacteriostatic and is capable of being maintained as such by addition of minor amounts of conventional preservatives without loss of its important characteristics.

The simulated mucus substance can also act as a vehicle or carrier for added medicaments, to thereby serve a dual function.

The substance can moreover be applied to medical instruments and dried to remove the water solvent, enabling the instrument to be packaged ready for use with application of moisture to activate the lubricant. Typical medical instruments so treated include catheters, tracheoscopes, and suppositories.

The substitute mucus constitutes a polyacrylamide composition. Polyacrylamide is known to be polymerized from the acrylamide monomer

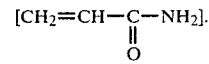

The polymer can be obtained from established supply houses such as the Dow Chemical Company under the trademark "SEPARAN". Basically, the material constitutes a water soluble high molecular weight polymer having a molecular weight in the range of about three million to about five million. The lower figure of about three million is perhaps more significant than the upper limit of five million since it is important that the molecular weight be sufficiently high to insure that the polymer particles cannot pass through a semi-permeable membrane. This insures that the polymer cannot pass through the skin and it insures that the material is not spermatocidal. It should preferably contain less than about 0.05% of acrylamide monomer to meet federal specifications on toxicity.

The particular high molecular weight "SEPARAN" polyacrylamide used is anionic in nature. Unmodified polyacrylamide is essentially nonionic, although a very small number, less than 0.5% of the amide groups are usually hydrolized to anionic carboxylic groups [—COO—Na+]. The anionic nature of the polyacrylamide polymer is increased typically by replacing additional amide groups with carboxyl groups, the resulting polymers represented by the following generalized structure:

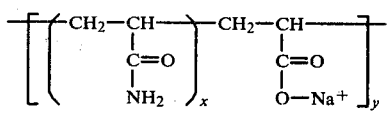

Approximately 26–36% of the amide groups are carboxyl substituted in this manner so that the polymer has about 26–36% of its appended groups in the form of a water soluble salt linkage with a cation such as sodium, the remainder of the appended groups being amides.

A preferred polyacrylamide which can be obtained from an established supply house such as the Dow Chemical Company is their trademark product "SEPARAN AP 273 Premium", the "premium" polymer being a potable water grade polymer which contains less than about 0.05% of acrylamide monomer. The polymer is, in its dry particulate form, a white, free flowing, anionic powder.

The material should be provided with a suitable preservative to be made bacteriostatic. Typical well-known preservatives can be employed, such as methyl p-hydroxy benzoate, propyl p-hydroxy benzoate, 4, 5 dibromo salicylanilide, and benzalkonium chloride. The use of a particular preservative is not essential to the performance of the product, as long as it exhibits no significant epidermal and mucousal toxicity, and possesses water solubility, compatibility with the other components, and functionality within the pH range encountered during storage and use. A suitable amount will vary somewhat depending upon the strength of the preservative and can readily be determined by known techniques. Typically, one part of preservative is added to about three to six parts of polymer.

The pH of the product is preferably adjusted to that normally encountered in the mucus secretions for which the product is being substituted. This polymer is stable in the useful pH range of about 3–10. For vaginal mucus substitution, the pH is adjusted to about 5–8, normally about 5, with a suitable acidic reagent or the like that has no significant epidermal or mucousal toxicity, such as citric acid or similar weak organic acids. Natural vaginal mucus has a normal pH of about 5, but this pH does vary a great deal such that the pH range of about 5–8 for the synthetic mucus is acceptable.

The ratio of polyacrylamide to water can be controlled to a practical range to obtain the desired lubricant. This range is controlled to obtain both characteristics of lubricity and pituitousness, as well as useful viscosity. The lubricity is evidenced at even very low concentrations, i.e. fractions of one percent of polymer to water. The concentration should be sufficiently high to obtain a viscosity sufficient to cause the material to adhere to the lubricated surfaces. This can be readily determined by simple experimentation. Usually, a minimum viscosity of about 1,000 centipoise is desirable, although viscosities as low as about 20 cp might be useful in some circumstances. The viscosity range of about 1,000–3,000 cp is preferred for normal vaginal usage. Higher viscosities can be readily achieved up to about 10,000 or even 13,000 cp by using a higher concentration of polymer to water, or by adding an inert viscosity increasing agent. Typically, the range of 0.30 to about 1.50 grams of polyacrylamide to 100 cc water is used. In some instances greater amounts can be employed. The higher the concentration, the greater the viscosity until ultimately the material is more gel-like. While these gel-like materials have limited usage, there are practical difficulties in preparing such because of difficulty in completely dispersing the polymer in the aqueous reagent. The most effective amount of polyacrylamide for use as a vaginal lubricant has been found to be about 0.75 g/100 cc water.

The total composition of the preferred version, which was the one also used most frequently, is:
polyacrylamide: 0.75 grams
preservative: 0.17 grams
 (methyl p-hydroxybenzoate: 0.15 grams)
 (propyl p-hydroxybenzoate: 0.02 grams)
water: 100 cc
To this was added a small amount of citric acid to adjust the pH to about 5.

In preparing the aqueous solution of polyacrylamide, it is basically important to obtain thorough dispersion of polymer particles in the water. This dispersion should be achieved within the first 2–3 minutes or so, because the polymer surfaces have a tendency to absorb water and become cohesive very quickly. The particles will tend to agglomerate during this period and prolonged agitation is then required to dissolve them. Good dispersion of the particles can be readily obtained mechanically, i.e. with agitation, or with other known techniques such as by the boiling water technique. This is done by dispersing the polymer particles into water while boiling, in which the particles are not soluble, and then lowering the water temperature for dissolution.

The substance also serves as an excellent vehicle for medicaments to be applied to the bodily surface area involved. The medicament, which is contained in minor amounts in the lubricant, can thus be applied uniformly and is retained in proper contact with the bodily surface for optimum effectiveness. The medicament so applied can function in several ways. Specifically, the composition can promote general well being, such as an antibiotic reagent in the substance would; it can prepare overly-sensitive surfaces for subsequent activity, such as a vaginal anesthetic agent in the substance would prior to sexaul intercourse or examination with medical instruments; it can render physical examination less uncomfortable to the patient such as by use of the composition with a fast acting anesthetic directly on the instrument; and others.

The medicaments could be any one or more of a variety of those available, such as anesthetic agents, estrogenic substances, antibiotic agents, steriods, and others, including combinations of these.

EXAMPLE 1

0.75 g of polyacrylamide particles were dispersed by agitation in 100 cc of water to which 0.15 g of methyl p-hydroxy benzoate and 0.02 g of propyl p-hydroxy benzoate was added as preservative. The pH was adjusted to 5 with citric acid. The resulting substitute mucus had excellent lubricity and pituitousness, exhibiting lubricious film forming and clinging characteristics. It was employed as a vaginal lubricant by smearing it on in typical finger painting manner, with excellent results.

EXAMPLE 2

This preparation, without pH adjustment, was also coated on a medical insertion instrument, a catheter, and used with excellent results.

EXAMPLE 3

The preparation in Example 2 was also coated on a series of catheters, and the lubricant coating was air dried to drive off the water portion. The catheter is then packaged and handled as normally, before needed. When needed, the catheter was remoistened, which caused the lubricant to resume its high quality condition. The catheter was then used with improved comfort for the patient, and with no mess or significant time required to achieve lubrication.

EXAMPLE 4

The composition in Example 2 was coated on a tracheoscope and air dried. The instrument was later remoistened and used with excellent facility.

At one time during the course of development of this product, it was thought that aqueous solutions of polyethylene oxide might also be acceptable alternatives to aqueous solutions of polyacrylamide polymers. However, it has been found that this is not true and that a distinct difference between the two solutions is ascertainable. Solutions of polyacrylamide in accordance with the present invention are crystal clear. There is a tendency for polyethylene oxide solutions to be cloudy and it is considerably more difficult to make them clear. The cloudiness gives the polyethylene oxide solutions an unacceptable appearance which would be repulsive or repugnant to many users.

Polyethylene oxide has a tendency to "salt out" during shelf life storage and during use. That is, it gets whitish or turbid. Further, the minute particles which "salt out" tend to make the solution irritating. This can happen during use and thereby defeat the purpose of the product. Such "salting out" does not occur with solutions of polyacrylamide made in accordance with the present invention.

It is also important that the polyacrylamide solutions made in accordance with the present invention can be sterilized in an autoclave. Autoclave sterilizing cannot be used on polyethylene oxide solutions. The "salting out" phenomenon discussed above is greatly aggravated during autoclaving. Thus, the only way to sterilize the solutions is by the more costly and time-consuming gas sterilization method. Gas sterilization is uneconomical for sterilizing large quantities of the solution.

It has also been found that there is a tendency for the polyethylene oxide solutions to become globby under some circumstances. This phenomenon is not encountered with polyacrylamide solutions made in accordance with the present invention.

Finally, in another important aspect of this invention, it has been found that instruments which have been coated with polyethylene oxide solutions, allowed to dry, sterilized and packaged, do not as readily rewet when they are subsequently remoistened. The important lubricating quality is not as readily regenerated by rewetting a polyethylene oxide coated instrument as it is by rewetting an instrument which has been coated with a polyacrylamide solution in accordance with the present invention.

The unique unexpected character of this material to serve as a solution to the physiological lubricant problem by serving as an excellent substitute physiological mucus for bodily orifices, particularly as vaginal and surgical lubricants, is remarkable. Also, various other materials could be added to the polyacrylamide solution, as to control color, odor, viscosity, pH, transparency, and the like, to name a few, provided that the additives did not significantly detract from the lubricity and pituitousness of the composition.

As noted, the composition can be employed as a carrier for other ingredients, particularly therapeutically active ingredients, e.g. penicillin, anesthetic agents, bacteriostatic reagents, or otherwise. The combination of a conventional anesthetic with the above noted components is particularly significant for relief from dysparunia, relief from discomfort caused by catherization, and the like.

The body-inserted medical instruments which can be coated with the substance, with or without added medicaments, are several, including catheters, tracheoscopes, endoscopes, and others, even suppositories.

Where the medical instrument is coated with the lubricant, and the lubricant is dried to remove the carrier, and subsequently rewetted just prior to use, the medicament, such as an anesthetic, can be added to the lubricant prior to drying, dried with the lubricant, and rewetted prior to use.

Additional advantages and features to those recited specifically herein may occur to others knowledgeable in the field upon understanding this disclosure. The invention is thus intended to be limited only as set forth in the following claims, and the reasonable equivalents thereto.

The embodiments of the invention is which an exclusive property or privilege is claimed are defined as follows:

1. A method of treating vaginal areas deficient in natural mucus, comprising the steps of:
   supplying a pituitous aqueous solution consisting essentially of about 0.3 to about 1.5 grams of polyacrylamide polymer per 100 cc of water, said polyacrylamide polymer having a molecular weight of at least about 3,000,000 and said solution having a pH in the range of about 3 to 10; and
   applying said solution to vaginal areas to form a stainless, odorless, nontoxic coating having lubricity, pituitousness and clingyness characteristics resembling those of natural vaginal mucus.

2. The method of claim 1 in which said polyacrylamide polymer contains less than about 0.05% of acrylamide monomer.

3. The method of claim 2 in which said aqueous solution includes a bacteriostatic agent.

4. The method of claim 3 in which said solution has a pH in the range from about 5 to 8.

5. The method of claim 4 in which said aqueous solution has a pH of about 5.

6. The method of claim 1 wherein said polyacrylamide polymer is an anionic polyacrylamide polymer.

7. The method of claim 6 in which said anionic polyacrylamide polymer has approximately 26-35% of its amide groups substituted by carboxyl groups.

* * * * *